United States Patent [19]

Sun

[11] 4,201,722
[45] May 6, 1980

[54] PROCESS FOR SEPARATING 4,4'-DIAMINODIPHENYLMETHANE

[75] Inventor: Kwok K. Sun, Hamden, Conn.

[73] Assignee: The Upjohn Company, Kalamazoo, Mich.

[21] Appl. No.: 693,081

[22] Filed: Jun. 4, 1976

[51] Int. Cl.$^2$ .............................................. C07C 85/26
[52] U.S. Cl. ................................................. 260/570 D
[58] Field of Search ........................... 260/570 D, 582

[56] References Cited

U.S. PATENT DOCUMENTS

| | | | |
|---|---|---|---|
| 2,149,525 | 3/1939 | Jenkins | 260/582 |
| 2,938,054 | 5/1960 | Demers, Jr. et al. | 260/570 |
| 3,175,007 | 3/1965 | Berhenke | 260/582 X |
| 3,996,283 | 12/1976 | Knofel | 260/570 |
| 4,029,705 | 6/1977 | Sayigh et al. | 260/570 |

Primary Examiner—Robert V. Hines
Attorney, Agent, or Firm—Denis A. Firth; John Kekich

[57] ABSTRACT

A process is described for the isolation of 4,4'-diaminodiphenylmethane in substantially pure form (of the order of 99% purity) from admixtures thereof with the corresponding 2,4'-isomer and 2,2'-isomer. The dihydrochloride of the isomeric mixture of diamines is heated in the presence of an inert organic solvent with a mixture of isomers of the free diamine, in which the amount of the 4,4'-isomer is at least equal to that of the 2,4'-isomer in the dihydrochloride isomeric mixture. The isomeric mixture of the diamines may be employed in the form of a mixture of polymethylene polyphenyl polyamines containing a major portion of said diamines. The reaction product consists of the insoluble dihydrochloride of substantially pure 4,4'-diaminodiphenylmethane and a solution which is enriched in 2,4'-isomer as compared with the starting mixture of diamines.

5 Claims, No Drawings

PROCESS FOR SEPARATING 4,4'-DIAMINODIPHENYLMETHANE

BACKGROUND OF THE DISCLOSURE

1. Field of the Invention

This invention relates to a process for separating isomeric diaminodiphenylmethanes and is more particularly concerned with the isolation of substantially pure 4,4'-diaminodiphenylmethane from admixture with the corresponding 2,4'-isomer.

2. Description of the Prior Art 4,4'-Diaminodiphenylmethane is a well-known compound which is useful as an intermediate in a number of reactions. For example, it is an intermediate in the preparation of polyamides such as nylon and in the preparation of the corresponding 4,4'-methylenebis(phenyl isocyanate) which latter is widely used in the preparation of polyurethane elastomers. The diamine is normally prepared by condensation of aniline and formaldehyde to yield a mixture of polymethylene polyphenyl polyamines in which the major component (40% by weight or higher) is diamine and from which the latter is isolated by, for example, distillation. The diamine so prepared is generally a mixture of the 4,4'-isomer in association with varying amounts of 2,4'-isomer and some 2,2'-isomer depending upon the particular method employed in its manufacture; see, for example, U.S. Pat. Nos. 3,362,979; 3,676,497 and 3,857,890.

For the various uses of 4,4'-diaminodiphenylmethane discussed above it is generally necessary to employ the compound in a substantially pure form. By "substantially pure" is meant that the diamine contains less than about 5 percent, and preferably less than about 2 percent, by weight of the corresponding 2,4'-isomer and or 2,2'-isomer. Various methods of achieving such a purity have been described. A commonly used method is fractional distillation under reduced pressure which normally involves some overall loss of material due to decomposition, polymerization and the like reactions which occur due to prolonged exposure to heat in the distillation kettle.

Canadian Pat. No. 745,173 describes the isolation of 4,4'-diaminodiphenylmethane in substantially pure state from the crude reaction product derived by condensation of aniline and formaldehyde in the presence of hydrochloric acid. The latter product is diluted with hot water and partially neutralized with alkali whereupon the substantially pure monohydrochloride of 4,4'-diaminodiphenylmethane crystallizes out upon cooling of the product. Because of the large volumes of solution required and other factors, the process is not suitable for adaption to continuous commercial operation.

British Pat. No. 1,169,127 describes the separation of 4,4'-diaminodiphenylmethane from admixture with its isomers by treating the mixture with an alkali metal or alkaline earth metal halide, cyanide or isothiocyanate, with which the 4,4'-isomer selectively forms an adduct, separating the adduct so formed, and regenerating the 4,4'-isomer from the adduct by heating with water or an inert solvent. Removal of last traces of the salt used to form the adduct is one of the drawbacks of this procedure which is not readily adaptable to commercial operation.

We have now found that the 4,4'-isomer of diaminodiphenylmethane can be readily separated from the corresponding 2,4'- and or 2,2'-isomers by a simple procedure which is readily adaptable to commercial production and which is free from the disadvantages noted above.

SUMMARY OF THE INVENTION

This invention comprises a process for separating 4,4'-diaminodiphenylmethane in substantially pure form from admixtures thereof with the corresponding 2,4'-isomer which process comprises:

heating, in the presence of an inert organic solvent, a mixture of (a) the dihydrochloride of said mixture of isomers and (b) a mixture of the 2,4'- and 4,4'-isomers of the corresponding free amines, the proportions of components (a) and (b) being such that the amount by weight of 4,4'-isomer of the free amine in component (b) is at least equal to the amount by weight of 2,4'-isomer in the dihydrochloride (a); and separating the insoluble, substantially pure, dihydrochloride of 4,4'-diaminodiphenylmethane from the reaction product.

DETAILED DESCRIPTION OF THE INVENTION

In carrying out the process of the invention it is possible to use, as the starting mixture of isomeric diamines, mixtures which contain from as low as 5 percent by weight of 4,4'-diaminodiphenylmethane up to as much as about 95 percent by weight of the latter, the remainder of said mixture being the corresponding 2,4'-isomer with usually minor amounts (up to about 5 percent by weight) of the 2,2'-isomer.

Component (a) of the reactants employed in the process of the invention, namely, the dihydrochloride of the mixture of isomers of the diamine to be separated, can be performed by any of the methods conventionally employed in the art for the conversion of amines to the hydrochloride. Illustratively, the diamine is dissolved in the stoichiometric amount of aqueous hydrochloric acid and the resulting solution is evaporated to dryness to recover the dihydrochloride. Another conventional method comprises treating a solution of the diamine in ether, tetrahydrofuran, or like ethereal solvents with a stoichiometric amount of ethanolic hydrogen chloride and isolating the dihydrochloride which precipitates.

Component (b) of the reactants employed in the process of the invention can be part of the same mixture of isomeric diamines, in the form of the free amines, as that employed to prepare the dihydrochloride of component (a) or it can be a mixture of a different composition having isomer ratios within the limits set forth above.

The proportions in which components (a) and (b) are brought together in carrying out the process of the invention are such that there is at least an equal amount by weight, and preferably an excess over this amount of the order of at least 5 percent by weight, of 4,4'-isomer in component (b) as there is 2,4'-isomer in the dihydrochloride of component (a). Thus, the process of the invention results in replacement of all, or substantially all, of the 2,4'-isomer in the dihydrochloride of component (a) by 4,4'-isomer from component (b). If there is insufficient 4,4'-isomer in component (b) to complete this exchange, the overall desired result will not be achieved.

The components (a) and (b) are brought together in the presence of an inert organic solvent. By the latter term is meant a solvent which does not enter into reaction with either of the components or otherwise interfere with the desired course of the reaction. Illustrative of inert organic solvents are benzene, toluene, xylene, chlorobenzene, decalin, dichlorobenzenes, cyclohexane and high boiling petroleum ethers. Advantageously, the inert organic solvent is one having a boiling point in the range of about 70° C. to about 180° C.

In carrying out the process of the invention the components (a) and (b) are heated together in the presence of the inert organic solvent at a temperature which is advantageously within the range of about 70° C. to about 140° C. although lower or higher temperatures can be employed if desired. The heating is continued, preferably with accompanying agitation, until analysis of an aliquot reveals that the diamine dihydrochloride, which remains as a solid precipitate throughout the reaction, is substantially pure 4,4'-isomer. Any conventional analytical technique such as gas chromatography can be employed for this purpose. When the reaction is adjudged to be complete by such analysis, the reaction mixture is cooled to room temperature (circa 20° C.) and the solid precipitate of substantially pure 4,4'-diaminodiphenylmethane dihydrochloride is isolated by filtration, centrifugation or like means.

The dihydrochloride so isolated can then be phosgenated as such using conventional phosgenation techniques to yield substantially pure 4,4'-diisocyanatodiphenylmethane. Alternatively, the dihydrochloride can be neutralized with sodium hydroxide, potassium hydroxide or like alkalies, to yield the free 4,4'-diaminodiphenylmethane in substantially pure form.

The mother liquor remaining after separation of the insoluble dihydrochloride as described above contains a mixture of isomers of the starting diamine which is richer in 2,4'-isomer than the starting mixture (b). If desired, the mixture can be recycled through the process of the invention to recover further amounts of pure 4,4'-isomer therefrom.

In a particular embodiment of the process of the invention the mixture of components (a) and (b) in inert organic solvent to be employed as starting materials can be generated in situ. This can be accomplished by dissolving the appropriate mixture of isomers of the diamine in the inert organic solvent and passing sufficient hydrogen chloride gas into the mixture as is necessary to convert the desired amount of diamine to dihydrochloride. The process of the invention is then carried out as before using the mixture of components (a) and (b) so generated.

The process of the invention, in addition to being useful in separating the 4,4'-isomer from admixture with the isomeric diamines per se, can also be applied to the separation of 4,4'-isomer from the isomeric diamines which are present as part of a mixture of polymethylene polyphenyl polyamines obtained by condensation of aniline and formaldehyde; see the art cited above. Advantageously, said polymethylene polyphenyl polyamines contain at least about 10 percent by weight of diamine and preferably contain from about 70 percent to about 95 percent by weight of diamine. In applying the process of the invention to selective isolation of 4,4'-diaminodiphenylmethane from such mixtures of polymethylene polyphenyl polyamines, one can employ the appropriate amount of the latter as component (b) or one can generate components (a) and (b) in situ by passing the requisite amount of hydrogen chloride gas into a solution of the polymethylene polyphenyl polyamines in the appropriate inert organic solvent.

The following example describes the manner and process of making and using the invention and sets forth the best mode contemplated by the inventors of carrying out the invention but is not to be construed as limiting.

EXAMPLE 1

To a solution of 2 g. (20.2 mmol.) of diaminodiphenylmethane (containing 15.4 percent by weight of 2,4'-isomer and 84.6 percent of 4,4'-isomer) in 15 ml. of methanol was added 4.2 ml. (42 mmol.) of 10 N hydrochloric acid and the resulting mixture was stirred for 30 minutes before being evaporated to dryness on a rotary evaporator. The residue was treated with 10 ml. of methanol and the mixture was again evaporated to dryness on the evaporator. The treatment with methanol followed by evaporation was repeated a second time. The final residue was recrystallized from a mixture of methanol and ether to obtain 2.4 g. of diaminodiphenylmethane dihydrochloride having a melting point of 277° to 279° C. (decomposition). A sample of diamine, regenerated from the dihydrochloride by neutralization with sodium hydroxide, was shown by vapor phase chromatography to contain 12.7 percent of 2,4'-isomer and 87.3 percent of 4,4'-isomer.

A mixture of 0.271 g. (1 mmol.) of the dihydrochloride so obtained, 0.396 g. (2 mmol.) of the diaminodiphenylmethane employed as starting material in the preparation of the dihydrochloride, and 1.5 ml. of chlorobenzene was heated under reflux for 2 hours. The resulting product was allowed to cool to 20° C. and filtered. The solid so isolated was washed on the filter with chlorobenzene and then with petroleum ether before being dried in vacuo. There was thus obtained 0.28 g. (1.03 mmol.) of diaminodiphenylmethane dihydrochloride having a melting point of 276.5° C. (decomposition). This dihydrochloride was neutralized with sodium hydroxide and the free diamine so isolated was found by vapor phase chromatography to contain 99.3 percent by weight of 4,4'-isomer and 0.7 percent by weight of 2,4'-isomer.

The filtrate from the above isolation procedure was evaporated to dryness to yield 0.401 g. (2.03 mmol.) of diaminodiphenylmethane which was shown by vapor phase chromatography to contain 76.3 percent by weight of 4,4'-isomer and 23.6 percent by weight of 2,4'-isomer.

I claim:

1. A process for separating 4,4'-diaminodiphenylmethane in substantially pure form from admixtures thereof with the corresponding 2,4'-isomer which process comprises:

heating in the presence of an inert organic solvent a mixture consisting essentially of (a) the dihydrochloride of said mixture of isomers, and (b) a mixture of 2,4'- and 4,4'-isomers of the corresponding free amines, the proportion of components (a) and (b) being such that the amount by weight of 4,4'-isomer of the free amine in component (b) is at least equal to the amount by weight of 2,4'-isomer in the dihydrochloride component (a); and separating the insoluble, substantially pure, dihydrochloride of 4,4'-diaminodiphenylmethane from the reaction product.

2. The process of claim 1 wherein the inert organic solvent has a boiling point in the range of 70° C. to 180° C.

3. The process of claim 2 wherein the inert organic solvent is chlorobenzene.

4. The process of claim 1 wherein the mixture (b) of the 2,4'- and 4,4'-isomers of the free amines comprises a mixture of polymethylene polyphenyl polyamines obtained by the condensation of aniline and formaldehyde and having a diamine content in the range of about 70 percent to about 95 percent by weight.

5. The process of claim 1 wherein the substantially pure dihydrochloride of 4,4'-diaminodiphenylmethane is separated from the reaction product by filtration and the free diamine is liberated therefrom by neutralization.

* * * * *

UNITED STATES PATENT OFFICE
CERTIFICATE OF CORRECTION

Patent No. 4,201,722　　　　　　　　　　Dated May 6, 1980

Inventor(s) Kwok K. Sun

It is certified that error appears in the above-identified patent and that said Letters Patent are hereby corrected as shown below:

Column 2, Line 35:　　　　　　Should Read:

performed　　　　　　　　　　preformed

Signed and Sealed this

Nineteenth Day of August 1980

[SEAL]

*Attest:*

SIDNEY A. DIAMOND

*Attesting Officer*　　　　*Commissioner of Patents and Trademarks*